United States Patent [19]

Sprague et al.

[11] Patent Number: 4,977,085

[45] Date of Patent: Dec. 11, 1990

[54] CLONING AND EXPRESSION OF YEAST STE13 AND DPP2 GENES ENCODING DIPEPTIDYL AMINOPEPTIDASE A AND B

[75] Inventors: George Sprague, Eugene, Oreg.; Ira Herskowitz; Jeremy Thorner, both of Berkeley, Calif.; David Julius, New York, N.Y.; Lindley Blair, Los Angeles; Anthony Brake, Berkeley, both of Calif.

[73] Assignee: The Board of Regents of the Univ. of California, Berkeley, Calif.

[21] Appl. No.: 584,619

[22] Filed: Feb. 29, 1984

[51] Int. Cl.$^5$ .................... C12N 9/48; C12N 15/00; C12N 1/20; C07H 17/00
[52] U.S. Cl. .................... 435/212; 435/172.3; 435/224; 435/255; 435/320; 536/27; 935/14; 935/28; 935/60; 935/69; 935/70
[58] Field of Search .................... 435/68, 172.3, 224, 435/255, 317, 253; 536/27; 935/14, 28, 6, 69

[56] References Cited

PUBLICATIONS

Ratzkin, B. et al., *Proc. Natl. Acad. Sci.*, vol. 74, pp. 487–491, Feb., 1977.
Julius, D. et al., *Cell*, vol. 32, pp. 839–852, Mar., 1983.
Glover, D., *Genetic Engineering Cloning DNA*, pp. 66–78, Chapman and Hall, London & New York, 1980.
Jones, E. W. in *Yeast Geneticss* (Eds., Spencer, Spencer & Smith), Springer Verlag, N.Y., pp. 167, 180–185, 1983.

*Primary Examiner*—Richard A. Schwartz
*Assistant Examiner*—Larry Millstein
*Attorney, Agent, or Firm*—Flehr, Hohbach, Test, Albritton & Herbert

[57] ABSTRACT

A method is provided for expressing the proteases dipeptidyl aminopeptidases A and B which are useful for processing precursor proteins. Genes controlling these proteases may be insdrted into appropriate vectors and transformed into cultures. The proteases may either be utilized to process precursor proteins in vivo or may be extracted from cultures and used to process precursor proteins in vitro.

26 Claims, 3 Drawing Sheets

CLONING AND EXPRESSION OF YEAST STE13 AND DPP2 GENES ENCODING DIPEPTIDYL AMINOPEPTIDASE A AND B

The present invention is directed to a method for expressing two different yeast dipeptidyl aminopeptidases in prokaryotic or eukaryotic cell cultures. In particular, the present invention is directed to the isolation and use of the yeast STE13 and DPP2 genes for the expression of dipeptidyl aminopeptidase A and B, respectively.

An important potential contribution of recombinant DNA technology is to permit the production of large quantities of medically important proteins (such as, interferon and human growth factors) which are difficult to isolate in usable quantities from natural sources. However, in order to produce large quantities of a particular protein, at least the following three requirements must be met: (i) the gene encoding the desired protein must be isolated and purified, (ii) that gene must be made to function in a conveniently grown organism, such as yeast or bacteria, and (iii) the protein product of the gene must be identical or substantially identical to the protein normally made in the organism from which the gene was isolated. The latter requirement may not be fulfilled if the method used to create the gene which may be may be expressed in yeast or bacteria leads to the formation of a protein product which contains extra amino acid residues at either the amino-terminal or carboxy-terminal ends. The latter requirement may also not be met in the normal product of the gene is a protein which is initially expressed as a larger precursor which must be subsequently processed to the mature, active form. Usually the organism from which the gene was isolated will process the precursor by protease enzymes. However, if these proteases are absent from yeast or bacteria or present in insufficient amounts, then production of large quantities of the desired mature, active protein product may not be possible.

The present invention provides a method for expressing two yeast protease enzymes dipeptidyl aminopeptidases A and B which may be used to solve the problem of protein processing. The present invention provides the capability of producing large amounts of such proteases in yeast where they are normally found only in limited amounts. The proteases may be used either in vivo in yeast or isolated from the culture and used as a reagent in vitro to process precursor proteins made and purified from other organisms.

It is therefore an object of the present invention to provide a process for producing dipeptidyl aminopeptidases A and B.

It is another object of the present invention to provide novel DNA molecules which control expression of the yeast dipeptidyl aminopeptidase A and B.

It is a further object of the present invention to provide vectors containing, STE13 and DPP2 respectively, which are capable of expression of dipeptidyl aminopeptidases A and B, respectively, when transformed into yeast cells.

It is another object of the present invention to provide transformant strains of yeast capable of expressing dipeptidyl aminopeptidases A and B.

These and other objects will be apparent from the following description and preferred embodiments.

The present invention provides a method for producing dipeptidyl aminopeptidases by isolating DNA molecules which control expression of dipeptidyl aminopeptidase A and B and inserting them into vectors which, when transformed into appropriate cell cultures such as yeast, are capable of expressing dipeptidyl aminopeptidases A and B in large amounts.

Figure 1:
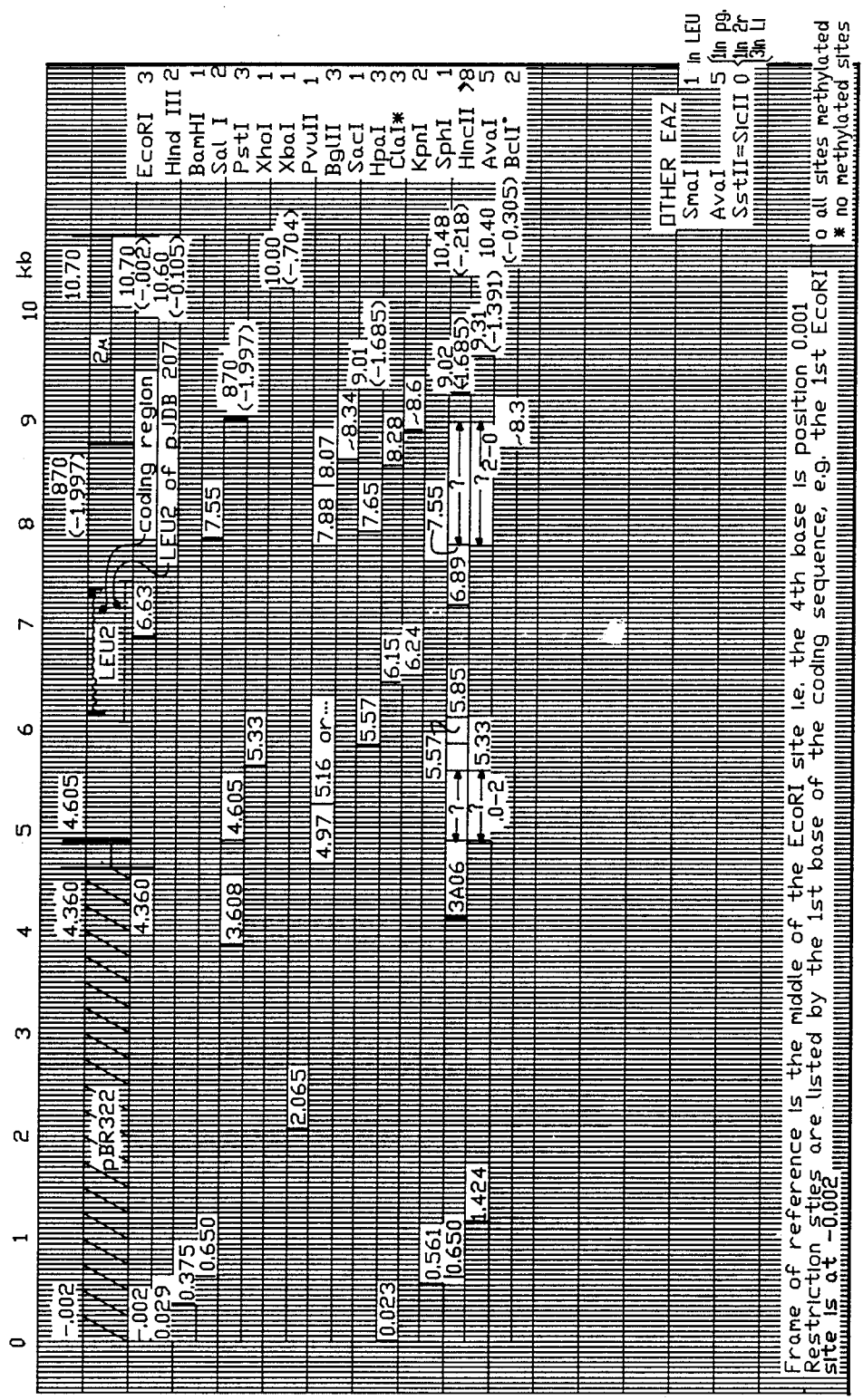
FIG. 1 is a restriction map of the plasmid vector YEp13.

Prior to setting forth the invention, it may be helpful to an understanding thereof to set forth definitions of certain terms to be used hereinafter.

Transformation means the process for changing the phenotype of a recipient cell mediated by the introduction of purified DNA. Transformation is typically detected by a stable inheritable change in the phenotype of the recipient cell that results from an alteration in either the biochemical or phenotypical properties of the recipient cell.

Chromosomal DNA means the DNA normally associated with histone in the form of chromosomes residing in the nucleus of a eukaryotic cell.

As used herein, a complementary DNA fragment (fDNA) is that DNA segment which complements a chromosomal DNA mutation.

The term vector as used herein means any piece of DNA which has been altered by human intervention or which is a clone of a piece of DNA which has been altered by human intervention, and which is capable of replication and transcription independent of replication and transcription of the host cell's chromosomal DNA (the genomic DNA). A vector will usually include a selectable marker which confers on the host organism one or more phenotypical properties which are different from the phenotypical properties of an untransformed host cell.

Expression is taken as its common meaning which is the ability of the host cell to produce a designated protein.

The yeast genes which control expression of dipeptidyl aminopeptidase A and B, respectively, are the genes STE13 and DPP2. These genes were isolated from a genomic (fDNA) library which was produced as follows. Yeast DNA from strain AB320 (ATCC No. 20817) was digested partially with Sau3A and fragments that range from 5-20 kilobase pairs in length were isolated by size fractionation on a sucrose gradient.

The digested DNA was then ligated into BamHI-digested YEp13 (also known as CV13, Broach et al, Gene 8, 121 (1979)), and transformed into E. coli cells. Plasmid DNA was prepared from the E. coli and then transformed into yeast MATα ste13 mutants (strain G150-15d, as identified by Sprague et al, J. Mol. Biol. 153, 323 (1981); ATCC deposit number 20808). Two different segments of genomic yeast DNA were isolated that complemented the ste13 mutation in vivo, in that the presence of these plasmids allowed the transformed cells to mate with MATa partners One of these plasmids, termed YEp13-GS13-3 containing the STE13 gene, completely suppressed the sterility of MATα ste13 mutants when integrated into the genome. A second plasmid, YEp13-GS13-4 containing the DPP2 gene, weakly suppressed the mating deficiency of MATα ste13 mutants when present as a multicopy plasmid. The two plasmids differed only in the nature of yeast DNA inserted at the BamH1 site in the Tet® gene in YEp13.

The plasmid containing the STE13 gene is apparently introduced into the yeast and maintained in multiple copies (20–50) in the yeast nucleus. Thus, the yeast strains which contain YEp13:STE13 (in the form of plasmid YEp13-GS13-3) overproduce (about 3 to 5 fold) dipeptidyl aminopeptidase A. This protease will degrade proteins by releasing glutamic acid-alanine, aspartic acid-alanine or alanine-proline dipeptide units from the amino-terminus. This enzyme may also remove any dipeptide of the sequence X-ala or X-pro, where X is any amino acid.

Similarly, the plasmid containing the DPP2 gene appears to be also present in the yeast nucleus in multiple copies (20 to 50) and to overproduce dipeptidyl aminopeptidase B by a factor of 10 to 15 fold. This protease will degrade protein sequentially by releasing dipeptide residues glutamic acid-alanine, aspartic acid-alanine and alanine-proline from the amino terminus This enzyme may also degrade peptide units different from those degraded by dipeptidyl aminopeptidase A.

The presence of either dipeptidyl aminopeptidase A or B may be assayed by treating yeast extracts with a synthetic substrate L-alanyl-L-prolyl-p-nitroanilide. The yeast extracts which release both p-nitroanilide (determined spectrophotometrically) and the dipeptide L-alanyl-L-proline (determined by thin-layer chromatography) from the substrate indicate the presence of the protease.

Referring to FIG. 1, there is shown the restriction map of YEp13.

Figure 2:
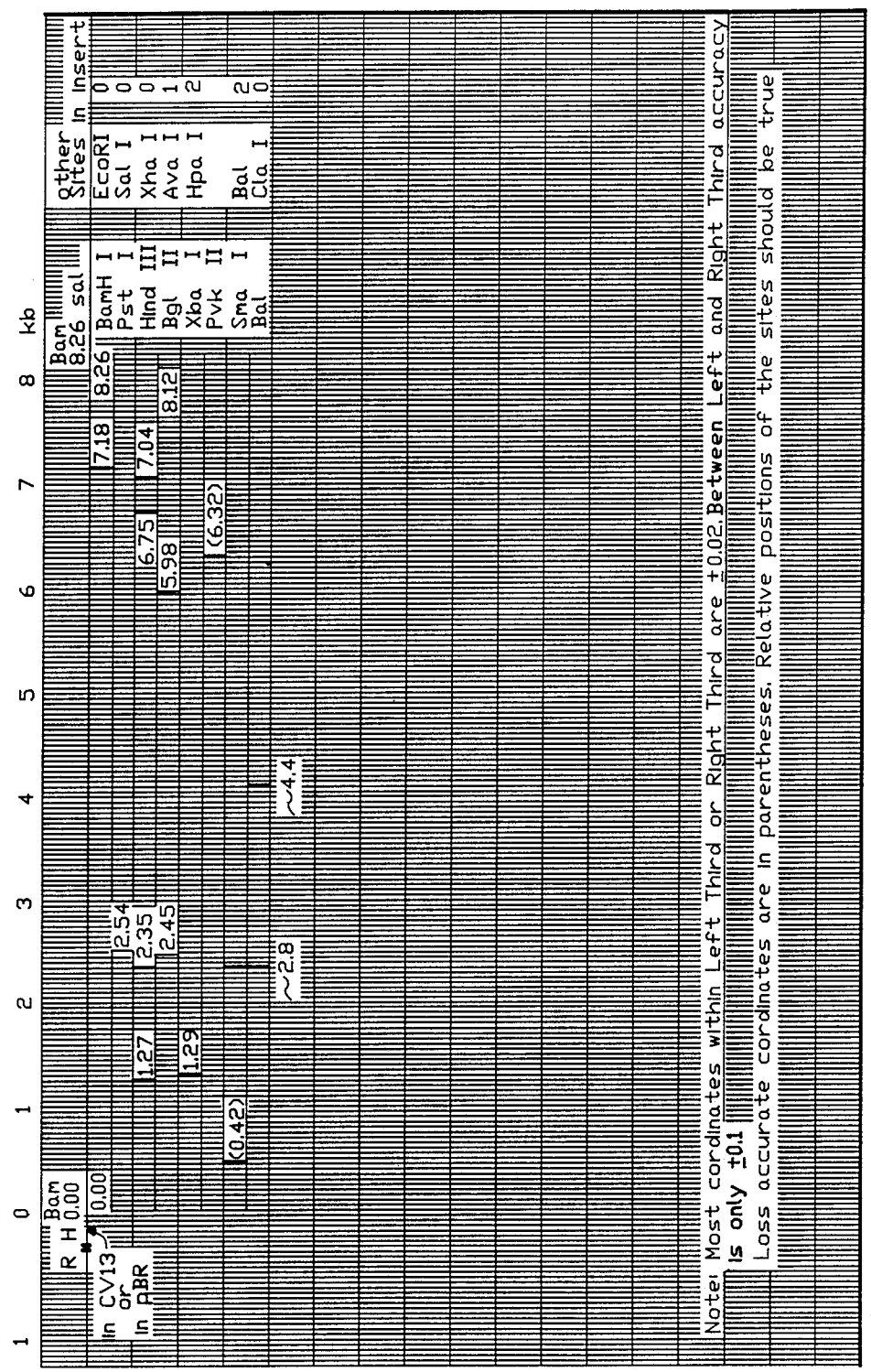
FIG. 2 is a restriction map of a DNA fragment containing the STE13 gene which controls the expression of dipeptidyl aminopeptidase A in yeast.

Referring to FIG. 2, there is shown the restriction map of the approximately 8.26 kb DNA fragment containing the STE13 gene which was inserted into vector YEp13-GS13-3.

Figure 3:
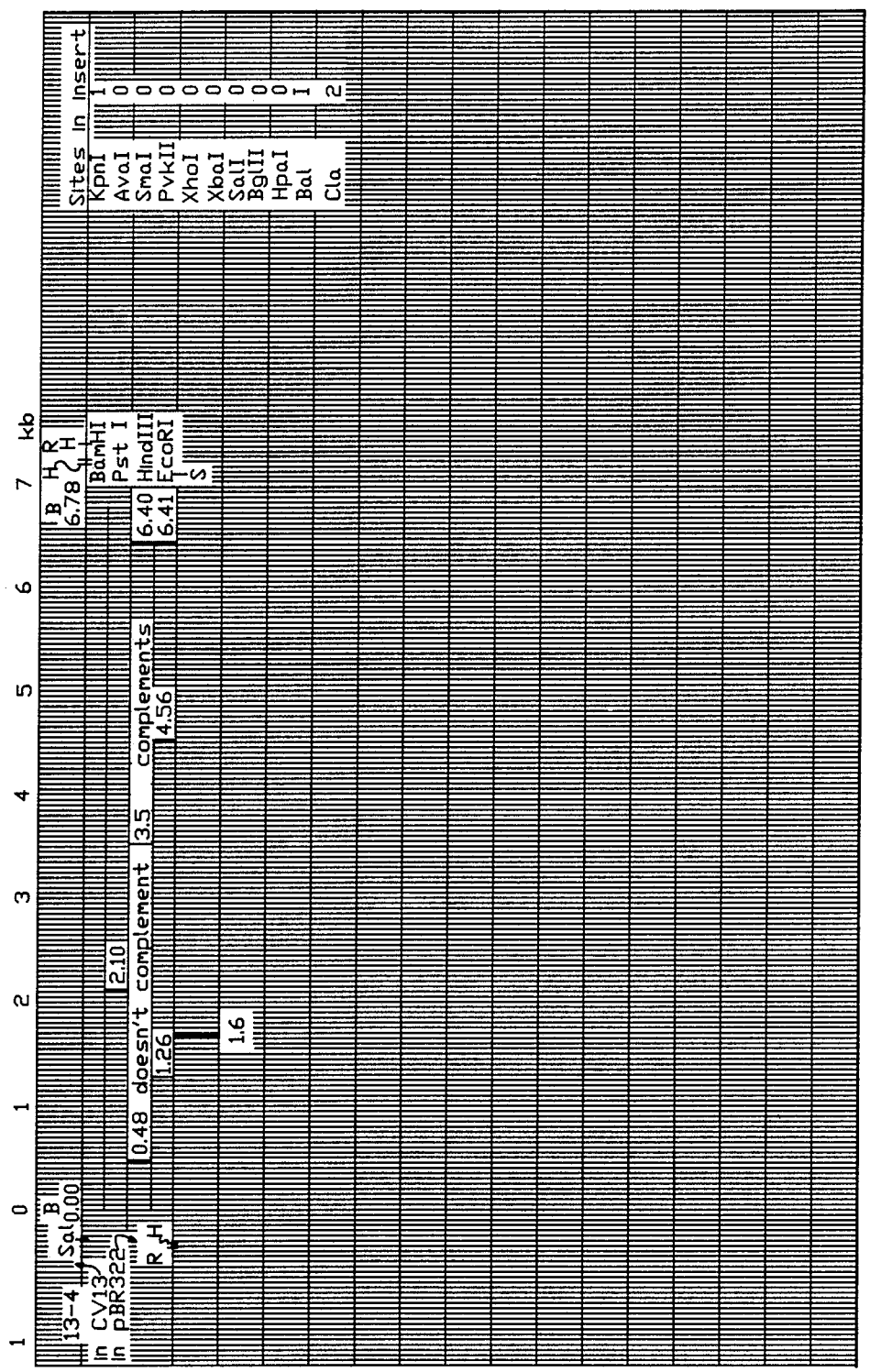
FIG. 3 is a restriction map of a DNA fragment containing the DPP2 gene which controls the expression of dipeptidyl aminopeptidase B in yeast.

Referring to FIG. 3, there is shown the restriction map of the approximately 6.78 kb DNA fragment containing the DPP2 gene which was inserted into plasmid YEp13-GS13-4

As shown, the DNAs in FIGS. 2 and 3 contain not only the STE13 and DPP2 genes, respectively, but also an indigenous yeast promoter which controls the expression of the protein or proteins encoded by the gene It will be readily apparent to those ordinarily skilled in the art that by exonucleasedigestion at the five prime end of each DNA segment, an appropriate number of base pairs may be removed up to and including the promoter sequence The resultant segment containing the gene without its indigenous promoter sequence may then be utilized by attaching other promoters, such as the promoter from the GAL 10 gene, which may be more active than the indigenous promotor in yeast or other desired host organisms.

It is also understood that the 6.78 kb and 8.26 kb fragments described herein will likely contain more bases than the respective DPP2 and STE13 genes. Hence, fragments containing less than about 6.78 kb and 8.26 kb, are deemed to be within the scope of the present invention, provided such smaller fragments contain the respective DPP2 and STE13 genes.

The DNA segments shown in FIGS. 2 and 3 may be inserted in vectors other than YEp13. Various vectors which are commonly used both in eukaryotic systems (such as yeast) and bacterial systems are well known in the art. As shown in FIGS. 2 and 3, the DNA segments have sticky BamHI ends, but these may be converted to any appropriate sticky end or to a blunt end by standard techniques. In this manner, the DNA segments shown in FIGS. 2 and 3 may be inserted into appropriate restriction sites in known vectors.

Such other vectors include YEp24, YRp7 and YCp50 (for use in yeast) and pBR322, pMB9 and pAS1 (for use in bacteria).

Additionally, the DNA structural genes may be inserted into vectors and transformed into tissue cultures, such as by the technique of Southern and Bery, J. Mol. Appl. Gen. 1, 327 (1982).

The methods of transformation of vectors into yeast, bacteria, and tissue cultures are known. See, for example, Beggs, *Nature* 275, 104 (1978); Clewell and Helinski, *Proc. Natl. Acad. Sci. (USA)* 62, 1159 (1969), Wigler et al., *Cell* 11, 223 (1977), and Mandel et al., *J. Mol. Biol.* 53, 154 (1970).

There are at least two methods for utilizing the proteases made according to the present invention. First, a vector containing a gene causing overproduction of dipeptidyl aminopeptidase A or B may be transformed into a cell culture which produces a protein that requires processing by a protease. In particular, it would be desirable to produce a transformant which produces a large amount of a precursor protein as well as a large amount of a protease according to the present invention, thereby enhancing the productivity of the transformant. The gene for the protease may be in its own vector or may be present in a vector together with the gene for the precursor protein which is to be processed. Examples of proteins which are known to require processing by dipeptidyl aminopeptidase A or B include prepro α-factor, and honeybee prepro-mellitin. Other proteins which may require processing by dipeptidyl aminopeptidase A or B-like enzymes include rat and human prepro-calcitonin, porcine prepro-beta-neoendorphin/dynorphin, human or bovine prepro-enkephalin, somatostatin, bovine ACTH, bovine prepro-opiomelanocortin, winter flounder prepro-antifreeze protein, and other hormone and peptide toxins.

The proteases produced according to the present invention may also be utilized for in vitro processing of proteins. For example, extracts may be taken from a transformant strain which overproduces either dipeptidyl aminopeptidase A or B and mixed with extracts from another culture which overproduces a precursor protein.

Having described the preferred embodiments, the following illustrations are given by way of example and are not intended to limit the invention.

EXAMPLE 1

Peptidase Activity in Transformants

The yeast strain XBH40-30B(MATα ste13-1) (ATCC No. 20810) was transformed with vector YEp13-GS13-3 (ATCC No. 20815) described above containing the STE13 gene allowing overproduction of dipeptidyl aminopeptidase A. MATα ste13 mutant will produce an inactive partially processed α-factor precursor protein, but not a mature α-factor, as determined by a biological assay (halo test). However, by transforming with YEp13-GS13-3, the transformant yielded a pronounced halo on MATa sst1 lawn, whereas control cells transformed with YEp13 did not. This assay for α-factor was conducted on a plate which was seeded with yeast haploid MATa cells. MATa haploid yeast are the normal types for the α-factor hormone. The MATa cells respond to α-factor by arresting growth. Therefore, a clear zone develops in the area immediately surrounding heavy patches or colonies of α-factor producing strains transferred to the plate as a result of the lack of proliferation of the MATa cells near the α-factor source while the remainder of the lawn grows out. Tester MATa strains (See Table 2) were used that carry mutations that make MATa cells hypersensitive to α-factor. Mutations at the SST1 locus make MATa cells 10–30 times more sensitive to the pheromone than normal MATa cells, because they are unable to inactivate the molecule by proteolytic degradation. Mutations at the SST2 locus makes MATa cells 100–300 times more sensitive to α factor than wild-type MATa cells.

As a second indication that ste13 transformants transformed with YEp13-GS13-3 produce α-factor, it was found that the α-factor produced by such transformants was fully biologically active without prior treatment with V8 protease, unlike the α-factor produced by control ste13 cells transformed with YEp13.

Also ste13 cells transformed with YEp13-GS13-3 plasmid regained and overproduced dipeptidyl aminopeptidase A activity three to five fold, depending upon the particular transformant and preparation examined.

Wild-type cells transformed with the plasmid also produced dipeptidyl aminopeptidase A to the same degree Normal cells (Tab. 1) transformed with YEp13-GS13-4 plasmid overproduced dipeptidyl aminopeptidase B even more dramatically. However, MATα ste13 mutant cells transformed with YEp13-GS13-4 plasmid (ATCC No. 20816) showed a modest increase in dipeptidyl aminopeptidase B activity. The results are summarized below in Table 1.

then pooled and separated according to size on sucrose gradients as described by Maniatis et al. Cell 15, 687 (1978), and fragments between 5 and 20 kb were ligated with vector YEp13 DNA that had been digested with BamHI YEp13 and bacterial alkaline phosphatase (the respective DNA concentrations were 50 and 10 μg/ml). After ligation, the DNA was made 20 mM in EDTA (pH 8.0) and used to transform E. coli strain RRI to ampicillin resistance (Amp®); 0.1 ml of ligation mixture produced $8.2 \times 10^4$ Amp® colonies, of which half were tetracycline sensitive (Tet$^S$). Plasmid DNA was prepared from a random 10 of the latter, and all were shown to contain a yeast DNA insert by an analysis of their restriction patterns with EcoRI. The average size of this sample of inserts was ≧7.5 kb. The transformant colonies were scraped from the ampicillin plates and the cells were pooled and pelleted by centrifugation. Half were stored in several aliquots as described by Beggs Nature 275 104 (1978) at −70° C. and the other half in 10 mM MgCl$_2$/50% (vol/vol) glycerol at −20° C.

Plasmid DNA was used to transform strain G150-15D (MATα leu2-3 leu2-112 his4 ste13-1) to leucine prototrophy. Two transformants which carried a plasmid able to complement the mating defect caused by the ste13-1 mutation were identified from 20,000 total transformants DNA was prepared (Nasmyth et al, PNAS USA 77 2119 (1980)) from both transformants and used to transform E. coli to ampicillin resistance. Plasmid DNAs were prepared from bacteria and used for restriction analysis and analysis and transformaton of yeast. Characterization of the genomic DNA inserts in these two plasmids revealed that they did not share common sequences. The two plasmids are designated YEp13-GS13-3 and YEp13-GS13-4. The insert fragment from YEp13-GS13-3 targets integration at the chromosomal STE13 locus and therefore the fragment contains the STE13 gene. In contrast, the insert fragment in YEp13-GS13-4 targets integration at a chromosomal location distinct from the STE13 locus. YEp13-GS13-4 therefore carries a yeast gene, referred to herein as DPP2 other than STE13 which nonetheless complements the ste13-1 mutation.

TABLE 1

| | Dipeptidyl Aminopeptidase Activities in Cells Transformed with Cloned Genes | | | |
|---|---|---|---|---|
| | | Specific Activity of DPAPase$^a$ | | Heat Stability of DPAPase (% of |
| Strain | Plasmid | Units/mg | Relative Level | Total)$^b$ |
| Permeabilized Whole Cells | | | | |
| AB35-14A (MATα STE 13) | YEp13 | 120 | [1] | 50 |
| | YEp13-GS13-3 | 480 | 4.0 | 107 |
| | YEp13-GS13-4 | 1,300 | 10.8 | 7 |
| XBH40-30B (MAT α ste13) | YEp13 | 70 | [1] | 1 |
| | YEp13-GS13-3 | 200 | 2.9 | 68 |
| | YEp13-GS13-4 | 100 | 1.4 | 1 |
| P100 Membrane Fraction | | | | |
| AB35-14A (MAT α STE13) | YEp13 | 13,780 | [1] | 30 |
| | YEp13-GS13-3 | 46,850 | 3.4 | 73 |
| | YEp13-GS13-4 | 84,880 | 6.2 | 4 |
| XBH40-30B (MAT α ste13) | YEp13 | 7,430 | [1] | 2 |
| | YEp13-GS13-3 | 17,830 | 2.4 | 52 |
| | YEp13-GS13-4 | 11,150 | 1.5 | 3 |

$^a$Units are defined as picomoles of Ala-Pro-pNA hydrolyzed per minute as 35° C. either by permeabilized whole cells or by partially purified membranes, prepared as described in the Experimental Procedures. Specific activity for permeabilized cells is expressed per milligram of cells; for membrane fractions, per milligram of protein.
$^b$Ratio of the rate of hydrolysis of the substrate art 37° C. following a preincubation at 60° C. for 15 min, compared with the rate of an identical sample preincubated at 37° C. prior to assay.

EXAMPLE 2

Preparation of Yeast DNA Library and Insertion into YEp13

Construction of a Pool of Yeast DNA Sequences in YEp13. Unless otherwise stated, all cloning procedures involving E. coli were as described by Goodman et al. P.N.A.S. USA, 74 5453 (1977). Yeast DNA from AB320 was partially cleaved with three different concentrations of Sau3A (0.5, 1.0, and 2.0 relative units) so that its average size was approximately 10 kilobases (kb). It was

EXAMPLE 3

Assay of Dipeptidyl Aminopeptidase

Measurement of peptidase activity was carried out by minor modifications of the procedure of Suarez-Rendules et al. *FEBS Lett.* 131,296 (1981). To distinguish between peptidase A and B, assays were performed before and after heat treatment. Heat treatment was conducted by incubating a reaction mixture, prior to substrate addition, at 60° C. for 15 minutes. Samples were then equilibrated to 37° C. for 5 minutes before initiation of reaction. The assays were strictly linear both with respect to time (for at least 1 hr) and with respect to either cell concentration (up to $5 \times 10^7$/ml) or concentration of membrane protein (up to 1 mg/ml), as long as absorbance did not exceed 0.7 (about 25% conversion of total substrate added).

To prepare cells for assay, the strains to be tested were grown to late exponential phase (200 corrected Klett units) at 30° C. in YPD, or in SC-Leu for transformed strains, harvested by centrifugation, washed once with 0.9% NaCl (15 ml/g wet weight) and then frozen at $-76°$ C. To prepare permeabilized cells, cell pellets were thawed on ice and resuspended in 50 mM potassium acetate (pH 5;2.5 ml/g wet weight), and the nonionic detergent Brij 58 was added to a final concentration of 1%. To complete permeabilization, cells were left on ice for at least 30 minutes prior to use. Membrane fractions were obtained by minor modifications of the method of Suarez-Rendueles et al. (1981). The resulting pellet material from a 100,000 $\times$ g centrifugation was resuspended in 50mM potassium acetate (pH 5) to give a final protein concentration of 5-10 mg/ml. At least 75% of the total peptidase activity of the whole-cell lysates was found in this crude membrane fraction (P100, See Table 1).

The protein concentration of both permeabilized cells and membrane preparations was determined by the method of Bradford *Anal. Biochem.* 72 248 (1976), after solubilization by boiling for 3 minutes in 0.1% SDS, 1% 2-mercaptoethanol and 50 mM Tris-HCl (pH 7.5), followed by centrifugation for 2 minutes in a microfuge to remove any insoluble material. Bovine serum albumin was the standard.

EXAMPLE 4

Pheromone Bioassay and Radioimmunoassay

To follow the biological activity of $\alpha$ factor a "halo" assay was used, which is an agar diffusion assay in which the radius of the halo of growth inhibition is proportional to the logarithm of the initial concentration of $\alpha$-factor applied to a filter disk. To follow production of $\alpha$-factor antigens, a radioimmunoassay was used. The generation of the anti-$\alpha$- factor antiserum, the recognition properties of these antibodies and the conditions and procedures for the radioimmunoassay are similar to those described in Brake, et al., *Mol. Cell. Biol.* 3, 1440 (1983) and Emter, et al. *Biochem. Biophys. Res. Comm.* 116 822 (1983).

To concentrate and partially purify $\alpha$-factor-related peptides for both bioassay and radioimmunoassay, the various yeast strains to be tested were grown at 30° C. with vigorous aeration in SD with appropriate supplements, or in SC-Leu for transformed strains, to late exponential-early stationary phase ($1 \times 10^8$/ml), and the cells were removed by centrifugation. The cell-free culture fluid was passed using gentle aspirator suction through a small bed of Bio-Rex 70 (1 ml resin/50 ml culture fluid) in a disposable column that had been previously equilibrated with 0.1N acetic acid. The column was washed with 2 bed volumes each of 0.1N acetic acid and 0.5M pyridine-acetate (pH 4.2). The $\alpha$-factor-related peptides were eluted with 2 bed volumes of 3.5M pyridine-acetate (pH 5.5). Samples of the eluate (1-100 $\mu$l) were dried in a vacuum oven at 37° C. in disposable thick-walled test tubes (10$\times$75 mm) and were analyzed directly by radioimmunoassay. Other portions (1 ml) of the same eluates were taken to dryness under vacuum in a centrifugal concentrator (Savant Speed-Vac) at 37° C. and redissolved in an appropriate volume of 0.1 N acetic acid. For bioassay, the redissolved material was adjusted to a final concentration of 4 $\mu$g $\alpha$-factor-crossreacting material per milliliter by dilution with 0.1 sodium acetate (pH 3.5) and spotted onto filter discs.

EXAMPLE 5

Purification of Pro-$\alpha$-Factor ("$\alpha$-Factor*")

Cells of A2S3 (Table 2) were used to inoculate 36 liters of SD with appropriate supplements to a cell density of about $10^5$/ml, and were grown with vigorous aeration at 25° C. in a fermenter (New Brunswick Fermacell). Cell growth was followed turbidometrically using a Klett-Summerson photoelectric colorimeter (#66 red filter) Under the conditions used, doubling time was approximately 4 hr. Twenty-two hours after inoculation (120 corrected Klett units), p-tosyl-L-arginine methyl ester, which impedes $\alpha$-factor proteolysis (Ciejek and Thorner, *Cell* 18.623, 1979; Thorner "Molecular Genetics of Development". W. A. Loomis and T. J. Leighton, eds., Academic Press, N.Y. 1980, pp 119-178), was added to a final concentration of 1 mM. Approximately 3 hr after the culture reached stationary phase (350 corrected Klett units) ethylene diamine tetraacetate (EDTA) and 2-mercaptoethanol, which reduce the rate of oxidation to methionine sulfoxide of the methionine residue in position 12 of $\alpha$-factor, were added to final concentrations of 1 mM and 5 mM, respectively. The culture was immediately chilled in crushed ice, and the cells were removed using an air-driven supercentrifuge (Sharples).

The cell-free culture fluid was passed through a bed (250 ml) of Bio-Rex 70, which had been previously equilibrated with 0.1 acetic acid, in a large Buchner funnel at a rate of 500 ml/min using gentle aspirator suction. The resin was washed successively with 700 ml each of 0.1 N acetic acid, 30% ethanol and 0.5 M pyridine-acetate (pH 4.2). All of these wash solutions also contained 1 mM 2-mercaptoethanol and 1 mM EDTA. The resin was eluted with 700 ml of 3.5 M pyridine-acetate (pH 5.5) containing 1 mM 2-mercaptoethanol and 1 mM EDTA. The eluate was adjusted to a final concentration of 2.5 M acetate by the addition of glacial acetic acid, and then concentrated to a final volume of 5 ml by rotary evaporation. The amber- colored viscous concentrate was diluted with 30% acetic acid until all the material appeared to be in solution. Just prior to ion-exchange chromatography, the sample was adjusted to a conductivity equivalent to that of 0.25 M acetic acid by the addition of distilled H$_2$O. The diluted material was applied at a rate of 0.5 ml/min to a bed (50 ml) of phosphocellulose (Whatman P-11) previously equilibrated with 0.25 N acetic acid and packed under pressure in a column (1.5$\times$27 cm). After sample application, the column was washed with 4 bed volumes of 0.25 N acetic acid, then eluted using from 0.25 N acetic acid to 2.0 M pyridne-acetate (pH 5.5). Fractions of 1.5 ml were collected. The pheromone-containing fractions, as judged by both radioimmunoassay and bioassay, eluted as a single major peak. These fractions were pooled and taken to dryness by rotary evaporation. This material was redissolved in 2 ml of 30% acetic acid containing 1 mM 2-mercaptoethanol and 5% glycerol and subjected to gel filtration through a bed (140 ml) of Sephadex G-25 (fine) in a column (1.5×90 cm) equilibrated with 30% acetic acid. The column was eluted with the same solvent at a rate of 0.3 ml/min, and 2 ml fractions were collected. The pheromone-containing fractions were pooled, taken to dryness and redissolved in 1.5 ml of 30% acetic acid containing 1 mM 2-mercaptoethanol.

The material was subjected to gel filtration through a bed (140 ml) of Sephadex G-50 (fine) in a column (1.5 x 90 cm) equalibrated with 30% acetic acid, eluting at a rate of 0.2 ml/min and collecting 1 ml fractions. At this stage, only a single peak of ultraviolet-absorbing material was observed, which co-eluted with both the biological activity and the α-factor-crossreacting material. The pheromone-containing fractions were pooled and stored at -20° C.

An overall yield of approximately 40% of the total α-factor-related peptide from the Bio-Rex 70 step was recovered in the final pooled Sephadex G-50 fractions, representing about 1.3 mg of purified α-factor.* Further resolution of the α factor* peptides was achieved using reverse-phase HPLC. Samples of purified factor* from the Sephadex G-50 pool (about 20 μg) were taken to dryness in a vacuum oven at 37° C., redissolved in 100 μl of 0.1% H and injected onto a column (4.1×25 mm) containing a reverse-phase C18 adsorbant (Synchropak RP-P) that had been equilibrated in 0.1% H containing 0.5% acetonitrile. Elution was performed at 1 ml/min with a linear mobile-phase gradient from 0.1% $H_3PO_4$ containing 0.5% acetonitrile at 0 min. to 0.045% $H_3PO_4$ containing 55% acetonitrile at 80 min. using a two-pump system (Perkin-Elmer; series 3B). Peptides were detected by absorbance at 220 nm using an on-line spectrophotometer (Perkin- Elmer; LC75). When α-factor* peptides were separated by HPLC on a preparative scale for subsequent analysis, removal of phosphoric acid from the samples was achieved by desalting through a bed (ml) of Sephadex G-10 that had been previously equilibrated with 30% acetic acid in a column (0.8×20 cm). Typically, the yield of peptide eluted from the HPLC column was 30%–50% of the material initially injected.

EXAMPLE 6

Organisms and Growth Conditions

The yeast strains used herein are given in Table 2. The compositions of rich broth medium (YPD), defined minimal medium (SD) and selective medium (SC-Leu) for the propagation of yeast strains harboring the plasmid YEp13 have been described previously (Sherman et al., "Methods in Yeast Genetics" (Cold Spring Harbor, N.Y.) 1979).

TABLE 2

| Strain | Genotype |
| --- | --- |
| XT1172-S245C | MATα ade6 his6 met1 leu1 trp 5 gal2 can1 rme1 |
| A2S3 | MATα ste13-1 ade6 his6 met1 leu1 trp5 gal2 can1 rme1 |
| RC634 | MAT a sst1-3 ade2 his6 met1 ura1 rme1 |
| RC687 | MATa sst2-4 ade2 his6 met1 ura1 rme1 |
| AB35-14A | MAT α leu2-3, 112 ura3-52[a] |
| XBH40-30B | MAT α ste13-1 leu2-3, 112 ura3-52 his4 lys1 trp1 met CAN1 |
| 227 | MATa cry1 lys1 |
| AB320 | HO ade2-1, lys2-1 trp 5-2 leu2-1 can 1-100 ura 3-1 and/or ura1-1 met4-1 |
| G150-15d | MAT α leu2-3, 112 his4 ste13-1 |

[a]Constructed by a series of crosses to contain auxotrophic markers that permit spheroplast transformation by a variety of yeast plasmid vectors.

What is claimed is:

1. A DNA molecule containing the yeast STE13 gene which controls the level of expression of dipeptidyl aminopeptidase A.

2. A DNA molecule containing the yeast DPP2 gene which controls the level of expression of dipeptidyl aminopeptidase B.

3. A DNA molecule according to claim 1 comprising about 8.26 kb.

4. A DNA molecule according to claim 2 comprising about 6.78 kb.

5. A vector comprising a DNA fragment which controls the level of expression of and encoding yeast dipeptidyl aminopeptidase A, said vector capable of expressing said aminopeptidase in eukaryotic cells.

6. A vector comprising a DNA fragment which controls the level of expression of and encoding yeast dipeptidyl aminopeptidase A, said vector capable of expressing said aminopeptidase in prokaryotic cells.

7. The vector according to claim 5 wherein said eukaryotic cells comprise yeast.

8. A vector according to claim 5 wherein said eukaryotic cells comprise mammalian tissue.

9. A vector according to claim 7 further comprising DNA sequences of plasmid YEp13.

10. A vector comprising a DNA fragment which controls the level of expression of and encoding yeast dipeptidyl aminopeptidase B, said vector capable of expressing said aminopeptidase in eukaryotic cells.

11. A vector comprising a DNA fragment which controls the level of expression of and encoding yeast dipeptidyl aminopeptidase B, said vector capable of expressing said aminopeptidase in prokaryotic cells.

12. A vector according to claim 10 wherein said eukaryotic cells comprise yeast.

13. A vector according to claim 10 wherein said eukaryotic cells comprise mammalian tissue.

14. A vector according to claim 12 wherein said vector further comprises DNA sequences of the plasmid YEp13.

15. A vector according to claim 5 or 10 comprising a promoter which controls the expression of said dipeptidyl aminopeptidase.

16. A vector according to claim 15 wherein said promoter is from the GAL10 gene.

17. A transformant eukaryotic strain containing a vector according to claim 5 or 10.

18. A yeast transformant strain according to claim 17.

19. A yeast transformant strain according to claim 18 containing vector YEp13-GS13-3.

20. A yeast transformant strain according to claim 18 containing the vector YEp13-GS13-4.

21. A method of expressing yeast dipeptidyl aminopeptidase A in a eukaryotic cell culture comprising a step of transforming said culture with a vector capable of expressing said aminopeptidase.

22. A method according to claim 21 wherein said eukaryotic cell culture comprises yeast.

23. A method according to claim 21 wherein said vector is YEp13-GS13-3.

24. A method of expressing yeast dipeptidyl aminopeptidase B in a eukaryotic cell culture comprises a step of transforming said culture with a vector capable of expressing said aminopeptidase in yeast.

25. A method according to claim 24 wherein said eukaryotic cell culture comprises yeast.

26. A method according to claim 24 wherein said vector YEP13GS13-4.

* * * * *